(12) United States Patent
Yarborough

(10) Patent No.: US 7,906,149 B2
(45) Date of Patent: Mar. 15, 2011

(54) METHOD FOR TREATING ALLERGIC DERMATITIS

(75) Inventor: Cody L. Yarborough, Cleburne, TX (US)

(73) Assignee: Boval Company, L.P., Cleburne, TX (US)

( * ) Notice: Subject to any disclaimer, the term of this patent is extended or adjusted under 35 U.S.C. 154(b) by 230 days.

(21) Appl. No.: 11/754,052

(22) Filed: May 25, 2007

(65) Prior Publication Data

US 2008/0292682 A1 Nov. 27, 2008

(51) Int. Cl.
*A61K 35/12* (2006.01)
*A61K 35/16* (2006.01)
*A61K 35/14* (2006.01)
*A61K 35/54* (2006.01)

(52) U.S. Cl. ........ 424/520; 424/529; 424/530; 424/531; 424/581

(58) Field of Classification Search ................ 424/520, 424/529, 530, 531, 581
See application file for complete search history.

(56) References Cited

U.S. PATENT DOCUMENTS

| | | | |
|---|---|---|---|
| 4,259,318 A * | 3/1981 | Duhe et al. | 424/94.4 |
| 4,473,495 A | 9/1984 | Patterson | |
| 5,047,249 A * | 9/1991 | Rothman et al. | 424/543 |
| 5,116,964 A | 5/1992 | Capon et al. | |
| 5,376,667 A | 12/1994 | Somers et al. | |
| 5,620,527 A | 4/1997 | Kramer et al. | |
| 5,686,074 A | 11/1997 | Stewart | |
| 5,702,709 A * | 12/1997 | Schulz et al. | 424/401 |
| 5,767,109 A | 6/1998 | Sanchez et al. | |
| 5,821,047 A | 10/1998 | Garrard et al. | |
| 5,962,634 A | 10/1999 | Jameson et al. | |
| 6,036,966 A * | 3/2000 | Youssefyeh | 424/401 |
| 6,090,292 A | 7/2000 | Zimmermann et al. | |
| 6,423,746 B1 * | 7/2002 | Yarbrough et al. | 514/561 |
| 6,482,831 B1 | 11/2002 | Wynn et al. | |
| 6,660,901 B2 * | 12/2003 | Church | 602/48 |
| 6,667,026 B1 * | 12/2003 | Goldman et al. | 424/47 |
| 6,696,396 B1 * | 2/2004 | Arneson | 510/130 |
| 7,008,963 B2 | 3/2006 | Yarbrough | |
| 7,101,851 B2 | 9/2006 | Lowman et al. | |
| 2006/0257441 A1 | 11/2006 | Komai et al. | |
| 2006/0275333 A1 | 12/2006 | Trimble et al. | |

FOREIGN PATENT DOCUMENTS

EP 1762227 A2 3/2007

OTHER PUBLICATIONS

McClendon et al. ,Fire Ant Venom Alkaloid, Isosolenopsin A, a Potent and Selective Inhibitor of Neuronal Nitric Acid, International Journal of Toxicology, 22:81-86, 2003.*
Wiedermann, Anti-inflammtory activity of albumin, Critical Care Medicine, vol. 35 (3),pp. 981—Mar. 2007.*
McClendon et al.,Fire Ant Venom Alkaloid, Isosolenopsin A, a Potent and Selective Inhibitor of Neuronal Nitric Acid, International Journal of Toxicology, 22:81-86, 2003.*
Wiedermann (Anti-inflammatory activity of albumin, Critical Care Medicine, vol. 35 (3), pp. 981-982, Mar. 2007.*
McClendon et al. (Fire Ant Venom Alkaloid, Isosolenopsin A, a Potent and Selective Inhibitor of Neuronal Nitric Acid, International Journal of Toxicology, 22:81-86, 2003.*
Wiedermann, Anti-inflammatory activity of albumin, Critical Care Medicine, vol. 35 (3), pp. 981-982, Mar. 2007.*
Hawaii Ant Group, "The Red Imported Fire Ant (*Solenopsis invicta*): A Severe and Imminent Threat to Hawaii," Feb. 8, 2001.
Pierpoint, W.S., "o-Quinones Former in Plant Extracts," Biochem. J. (1969), 112, 609.
Ralston, James P., "Fire Ant Bites," www.emedicine.com, Jan. 17, 2006.
Yi, G. B. et al., "Fire Ant Venom Alkaloid, Isosolenopsin A, a Potent and Selective Inhibitor of Neuronal Nitric Oxide Synthase," Intl. J. of Toxicology, (2003), 22:81-86.
Zanfel Wash product detail, www.cvs.com, Nov. 6, 2006.
Bos, J. and Meinardi, M., "The 500 Dalton rule for skin penetration of chemical compounds and drugs," Experimental Dermatology (Jun. 2000), 9:165 (abstract).
Billich, Andreas et al., "Novel cyclosporin derivatives featuring enhanced skin penetration despite increased molecular weight," Bioorgg. med. chem. (1993), 13:3157 (abstract).
Decision on Appeal from the U.S. Patent and Trademark Office Board of Patent Appeals and Interferences dated Nov. 7, 2008 regarding U.S. Appl. No. 10/405,974.

* cited by examiner

*Primary Examiner* — Johann R Richter
*Assistant Examiner* — Kristie L Brooks
(74) *Attorney, Agent, or Firm* — Hayes and Boone, LLP

(57) ABSTRACT

A method for treating oleoresin induced allergic dermatitis by topically contacting an affected area with a therapeutically effective amount of one or more biopolymers for a sufficient amount of time to enable the one or more biopolymers to have an effect and removing the one or more biopolymers from the affected area. The oleoresin can be urushiol, isosolenopsin A, or a combination thereof. The one or more biopolymer can be albumin. The one or more biopolymers can provide a localized anti-inflammatory effect.

15 Claims, No Drawings

METHOD FOR TREATING ALLERGIC DERMATITIS

FIELD OF THE INVENTION

The present disclosure relates to the treatment of allergic dermatitis, and in particular to allergic dermatitis resulting from contact with naturally-occurring hydrophobic toxins such as urushiol and isosolenopsin A.

BACKGROUND OF THE INVENTION

Allergic dermatitis can be caused from contact with hydrophobic toxins found in plants, insects, and animals.

Urushiol is a commonly encountered hydrophobic toxin in the exudate of plants such as poison ivy, poison oak, poison sumac, and related plants in the Anacardiaceae group. Some experts estimate there are up to 55 million cases of urushiol-induced contact dermatitis annually in the United States. When adequately exposed to urushiol containing plants, it has been estimated that about 85 percent of all people will develop an allergic reaction.

Urushiols are mixtures of catechols with long, hydrophobic, carbon (alkyl) side chains at the three position of the catechol ring. Poison ivy contains predominately 3-n-pentadececylcatechols (C-15) and poison oak contains predominantly 3-n-heptaecylcatechols (C-17).

After exposure, urushiol binds to the skin causing a rash to develop within two days. The rash peaks in five days and can take two or more weeks to heal. Redness, swelling, blisters, and severe itching are typical urushiol-induced dermatologic reactions. The rash appears to spread when it breaks out in new areas. Urushiol is absorbed more slowly where the skin is thicker, such as on forearms, legs, and the body's trunk. Urushiol can be transferred by fingernails or animal fur and can remain on clothing, shoes, and tools for up to five years in moist climates.

The red imported fire ant (Solenopsis invicta) has invaded over 300 million acres in the United States. The red imported fire ant is aggressive and has a powerful sting that has caused the deaths of at least 80 people, injury to tens of thousands of people annually, and injury and death of wildlife, livestock, and pets.

Fire ant venom differs from other insect venoms, which are mostly proteinaceous solutions. Fire ant venom is a hydrophobic toxin that includes isosolenopsin A and some minor proteins. Isosolenopsin A is a water insoluble dialkyl piperdine alkaloid. The substitutions of the piperdine ring are long chain aliphatic members. Isosolenopsin A can induce the release of histamine and other vasoactive amines from mast cells, resulting in a sterile pustule at the sting site. The toxicity of isosolenopsin A is believed to cause the pustules to form. Large, local reactions can also cause edematous tissue compression that can compromise the vascular supply to the effected area.

Urushiol and isosolenopsin A are mixtures of long hydrophobic-chained molecules that readily oxidize and react with proteins. The toxins can exist in both native and oxidized states on dermal layers.

Treatment of oleoresin-induced allergic dermatitis has historically involved washing the exposed area with soap and water and/or applying an astringent such as alcohol or witch hazel. People tend to fail at fully removing the oleoresin toxin before it has bound to the dermal proteins of the skin.

Other treatments of oleoresin-induced allergic dermatitis consist of steroids, anti-inflammatory, and antihistamine compounds that temporarily treat the symptoms of the response but do nothing to remove the toxin, which initiated the response.

U.S. Pat. No. 7,008,963, U.S. Pat. No. 6,423,746; and EP Patent App. 1762227A2 disclose several compositions with an abrasive factor to remove oleoresins from the exposed areas. However, these compositions contain high levels of surfactants capable of chemically-induced sensitivity and dermatitis themselves.

Other attempts for toxin removal can be seen in U.S. Pat. Nos. 5,686,074 and 5,620,527, but both patents utilize agents that can cause dermatitis themselves.

The method described herein advantageously provides an improved method for treating allergic dermatitis caused by exposure to naturally-occurring hydrophobic toxins.

SUMMARY

Treating oleoresin induced allergic dermatitis can be achieved by topically contacting an affected area with a therapeutically effective amount of one or more biopolymers for a sufficient amount of time to enable the one or more biopolymers to have an effect and removing the one or more biopolymers from the affected area. The oleoresin can be urushiol, isosolenopsin A, or a combination thereof. The one or more biopolymers can provide a localized anti-inflammatory effect.

The one or more biopolymers can be delivered as a liquid, gel, cream, lotion, paste, ointment, foam, spray, mist, or aerosol to the affected area. Alternately, the one or more biopolymers are provided as a coating on, or a filler in a dressing, substrate or patch.

The one or more biopolymers can be albumin. In another embodiment the one or more biopolymers are selected from the group consisting of serum albumin, albumen, lipoproteins, and mixtures thereof. The biopolymer can be transferrin.

The one or more biopolymers can be provided in a biocompatible composition with one or more acceptable biocompatible carriers suitable for topical application to the affected area. The biocompatible composition can be one or more of a liquid, gel, cream, lotion, paste, or ointment containing the one or more biopolymer in an amount from about 0.1 to about 40% by weight.

The biocompatible composition can also include a pharmaceutically active ingredient such as, but not limited to, an analgesic, an antiasthmatic, an antimicrobial, an antipruritic, an antihistamine, an anti-inflammatory, an anti-skin wrinkling agent, a tanning active, a vasoconstrictor, a vasodilator, a vitamin substance, and mixtures thereof.

A drying agent and/or film former can be provided in the biocompatible composition.

DETAILED DESCRIPTION

As used herein and in the claims, the terms and phrases set out below have the meanings which follow.

"Affected area" means an area of skin exposed to a toxin.

"Albumen" is a protein found in the white of egg.

"Albumin" includes a group of simple proteins widely distributed in plant and animal tissues. They are found in blood as serum albumin, in milk as lactoalbumin, and in the white of egg as ovalbumin.

"Allergic Dermatitis" means inflammation of the skin caused by an allergy. A toxin can cause the allergy.

"Anti-inflammatory effect" means a reduction in one or more of the symptoms erythema (redness), edema (swelling), pain and pruritus which are characteristic of inflammation resulting from contact with a hydrophobic toxin.

"Biocompatible" means generating no significant undesirable host response for the intended utility. Most preferably, biocompatible materials are non-toxic for the intended utility. Thus, for human utility biocompatibility is most preferably non-toxic to humans or human tissues.

"Biopolymer" means a macromolecule of multiple repeating monomers produced by or derived from a living organism. The biopolymer can be albumin.

"Carrier" means a biocompatible vehicle including one or more solid, semisolid, or liquid diluents, excipients, or encapsulating substances.

"Lipoprotein" means any class of proteins that contain a lipid combined with a protein.

"Oleoresin" is a mixture of resin-containing oils secreted by plants and feeding insects. Oleoresin can be urushiol and isosolenopsin A.

"Serum Albumin" means a blood plasma protein. The human version is human serum albumin and the cattle version is bovine serum albumin.

"Therapeutically effective amount" is used herein to denote any amount of a formulation or composition having one or more biopolymers which will exhibit an anti-inflammatory effect, when applied to an affected area. The amount of active ingredient, that is the one or more biopolymers in the formulation, will vary with the type of toxin causing the allergic dermatitis.

"Toxin" means a hydrophobic toxin. The hydrophobic toxin can be an oleoresin such as, but not limited to, urushiol and isosolenopsin A.

"Transferrin" means a plasma glycoprotein.

The methods and formulations of the embodiments described herein can be applied to both humans and animals for treating allergic dermatitis resulting from exposure to a toxin.

It is believed that molecules having a molecular weight greater than approximately 500 Daltons are unable to pass the outer layer of the skin and are therefore unable to absorb into the skin (Bos and Meinardi, 2000). Other studies show that the limit may be increased to 1,600 Daltons by chemically modifying the molecules for absorption (Billich, et al., 2006). One or more biopolymers, hereinafter "biopolymer", are of a size and orientation that do not penetrate the dermal layers and, thus, remain topical. An embodiment provides that the biopolymer is bovine or human serum albumin, wherein each has an estimated molecular weight of about 66,500 Daltons (Peters, 1996).

The biopolymer is topically contacted such as by rubbing, smearing, spraying or placing the biopolymer on the dermal area exposed to the toxin. The biopolymer binds to the toxin in a competitive manner against the dermal proteins and can preferably bind to the toxin in both the native and oxidized states. By competing with the dermal proteins, the biopolymer can reduce the amount of toxin available to react with the dermal proteins.

After a sufficient time has elapsed such as, but not limited to, 30-60 seconds, the bound biopolymer and toxin can be removed. Removal can be accomplished by conventional rinsing methods. Conventional carriers such as, but not limited to, solvents and surfactants, can be used to facilitate removal of the biopolymer and bound toxin from the affected area.

The removal of the toxins from the dermal proteins can reduce the incidence of the inflammatory response while minimizing the removal of the protective lipids found on the skin. The reduction in the amount of toxin available to react with the dermal proteins can provide an anti-inflammatory effect.

An exemplary embodiment uses serum albumin as the biopolymer. One of the many functions albumin does in the bloodstream is to transport the numerous ligands such as fatty acids, hormones, steroids, metals, peptide. The molecule accomplishes this by binding of the moieties at several sites. Serum albumin is capable of reacting with numerous molecule types and able to transport the molecules while remaining soluble itself due to its structure. Albumin fractionation from blood and subsequent purification and chemical and physical modifications are current commercial processes that can help potentiate serum albumin.

In another exemplary embodiment, the biopolymer can be serum albumin, albumen, lipoproteins, and mixtures thereof.

A conventional means for dermally delivering a therapeutic substance can be used to topically contact the biopolymer to the affected area. An exemplary embodiment envisions that the biopolymer is in a liquid, gel, cream, lotion, paste, ointment, foam, spray, mist, or aerosol. Another exemplary embodiment provides delivering the biopolymer to the affected area as a coating on, or a filler in a dressing, substrate or patch.

The biopolymer can be provided in a biocompatible composition with one or more biocompatible carriers that are suitable for topical application to the affected area. The amount of the biopolymer in the biocompatible composition can vary depending on the toxin.

An exemplary embodiment of a biocompatible composition can contain about 0.1% to about 40% by weight of the biopolymer. Another example of a biocompatible composition can contain about 1 to about 20% by weight of a biopolymer. The biocompatible composition can contain about 1 to about 2, 3, 4, 5, 6, 7, 8, 9, or 10% by weight of a biopolymer.

The biocompatible carriers can assist with the stability of the biopolymer, preserve the formulation, and assist in removal of the biopolymer and toxin from the affected area. The biocompatible carrier can reduce the severity of the reaction and can assist in preventing secondary infections.

Suitable biocompatible carriers do no not react with the biopolymer and can be, but are not limited to a diluent, a chelating agent, a preservative, a thickener, a cosolvent, a humectant, and combinations thereof.

An exemplary embodiment of a formulation for a biocompatible composition is shown in Table 1.

TABLE 1

Formulation for treating allergic dermatitis resulting from exposure to an oleoresin.

| Ingredient | Percent by Weight |
| --- | --- |
| Diluent | QS |
| Biopolymer | 0.1–40 |
| Chelating agent | 0.01–0.1 |
| Preservative | 0.05–5 |
| Thickener | 0.01–10 |
| Co-solvent | 1.0–40 |
| Humectant | 1.0–10 |

Another example of a formulation for a biocompatible composition is shown in Table 2.

TABLE 2

Formulation for treating allergic dermatitis resulting from exposure to an oleoresin.

| Ingredient | Percent by Weight |
| --- | --- |
| Diluent | QS |
| Biopolymer | 2–6 |
| Chelating agent | 0.05–0.1 |
| Preservative | 0.05–1.0 |
| Thickener | 0.5–2 |
| Co-solvent | 2–6 |
| Humectant | 1.0–4.0 |

The diluent can be in a quantity sufficient (QS) to produce 100 percent by weight including the biopolymer and other carriers. The diluent can be aqueous although the embodiment is not limited thereto as other solvents, such as glycols and alcohols can be used.

A chelating agent can be used to bind and stabilize the biopolymer. The chelating agent can be disodium ethylenediamine tetraacetate (DS EDTA) or sodium citrate.

A preservative such as, but not limited to, methyl paraben can be used to maintain the integrity of the product. The preservative can have bacteriocidal and fungicidal properties.

A thickener can by used to achieve a desired viscosity and can form a barrier film on the skin. For example and not limitation, hydroxypropylcellulose can be used as a thickener. Hydroxypropylcellulose, such as Klucel, can be a medium viscosity cellulose-based polymer soluble in water, alcohol, or anyhydrous systems such as propylene glycol, can be used as a thickener. The invention also envisions using thickeners such as carbomers, polyvinyl alcohols, and polyvinyl pyrrollidones.

A cosolvent can be added to the biocompatible composition. The cosolvent can be, but is not limited to, polyethylene glycol, alcohols, and other glycols. The cosolvent can be a large molecule that can assist in the solubilization of urushiol.

A humectant can be used to retain the moisture content of the biocompatible composition when applied to the affected area. For example and not limitation, glycerine can be used as a humectant.

The biocompatible carriers can assist in the removal of the toxins from the dermal proteins and can reduce the incidence of the inflammatory response without removal of the protective lipids found on the skin.

The biocompatible composition can also include a pharmaceutically active ingredient such as, but not limited to, an analgesic, an antiasthmatic, an antimicrobial, an antipruritic, an antihistamine, an anti-inflammatory, an anti-skin wrinkling agent, a tanning active, a vasoconstrictor, a vasodilator, a vitamin substance, and mixtures thereof.

An embodiment provides an analgesic such as butamben picrate, lidocaine, xylocalne, benzocaine, bupivacaine, chlorprocaine, dibucaine, etidocaine, mepivacaine, tetracaine, dyclonine, hexylcaine, procaine, cocaine, ketamine, pramoxine, phenol, aloe vera, capsaicin, and mixtures thereof.

An antiasthmatic can be provided in the biocompatible composition and can be aminophylline, theophylline, orciprenaline sulphate, terbutaline sulphate, albuterol, salbutamol, and combinations thereof.

An embodiment has an antimicrobial agent in the biocompatible composition to assist in the prevention of secondary infections in the affected area. The antimicrobial agent can be an antifungal, an antibacterial, an antiseptic, and combinations thereof.

The antipruritic can relieve itching and can be, but is not limited to, include alclometasone dipropionate, betamethasone valerate, and isopropyl myristate MSD.

The anti-histamine can be histamine release inhibitors such as, but not limited to, diphenhydramine (Benadryl), chlorpheniramine, tripelennamine, promethazine, clemastine, doxylamine, and mixtures thereof.

The anti-inflammatory can be steroidal anti-inflammatory agents, non-steroidal anti-inflammatory agents, and mixtures thereof.

Non-limiting examples of steroidal anti-inflammatory agents suitable for use herein include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (flupred-nylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used.

Nonsteroidal anti-inflammatory agents are also suitable for use herein as skin active agents in the compositions of the invention. Non-limiting examples of non-steroidal anti-inflammatory agents suitable for use herein include oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (ASTRAZENECA and NicOx), Celecoxib (PHARMACIA Corp.) (4-[5-(4-methylphenyl)-3-(trifluoromethyl)-1H-pyrazol-1-yl]benzenesulfonamide), Meloxicam (BOEHRINGER INGELHEIM Pharmaceuticals) (4-hydroxy-2-methyl-N-(5-methyl-2-thiazolyl)-2H-1, 2GW-406381 (GLAXOSMITHKLINE), Etoricoxib (MERCK & Co.), Rofecoxib (MERCK & Co.) (4-[4-(methylsulfonyl)phenyl]-3-phenyl-2(5H)-furanone), Lumiracoxib (NOVARTIS Pharma AG), Valdecoxib (PHARMACIA Corp.) (4-(5-methyl-3-phenyl-4-isox-azolyl)benzenesulfonamide), Etodolac (WYETH Ayerst Laboratories) ((.±.) 1,8-diethyl-1,3,4,9-tetrahydropyrano-[3,4-b]acid, and combinations thereof.

The anti-skin wrinkling agent can be C2-C30 alpha-hydroxy acids (e.g., glycolic acid, lactic acid, 2-hydroxybutanoic acid, and the like), retinoic acid, salicylic acid, and mixtures thereof.

An embodiment includes a tanning agent in the biocompatible composition. The tanning agent can be dihydroxyacetone, glyceraldehyde, indoles and their derivatives, and mixtures thereof. A sunscreen agent can also be used in combination with the tanning agent.

An embodiment further includes a vasoconstrictor can include pharmaceutically-acceptable salts of dihydroergotamine, ergotamine, methysergide, and combinations thereof A vasodilator can be provided in the biocompatible composition such as, but not limited to, pharmaceutically-acceptable salts of diltazem, amiodarone, isoxsuprine, nylidrin, tolazoline verapamil, and mixtures thereof.

The vitamin can be, but the embodiment is not limited to, Vitamin A and derivatives thereof (including, for example, retinol, see anti-wrinkling actives), ascorbic acid (Vitamin C and derivatives), Vitamin B (e.g., riboflavin, vitamin B.sub.2), biotin, Vitamin D (all forms), Vitamin E and derivatives thereof such as tocopheryl acetate, beta-carotene, panthothenic acid and mixtures thereof.

An embodiment further includes a drying agent in the biocompatible composition such as, but not limited to, diethyleneglycolmonothylether.

Another embodiment can include a film former in the biocompatible composition such as polyvinylalcohol.

The embodiments described herein can provide relief for symptoms associated with allergic dermatitis caused by contact with natural toxins such as urushiol and isosolenopsin A.

The following examples are offered in order to more fully illustrate exemplary embodiments but are not to be construed as limiting the scope thereof.

EXAMPLE 1

A topical liquid was prepared using the formulation in Table 3 for treating allergic dermatitis.

A young male developed allergic dermatitis after being exposed to poison ivy. Approximately 3 mL of the topical liquid was applied to the affected area. The liquid was applied to the affected area in a circular rubbing motion. After 30 seconds, the liquid was removed with water. The pruritus subsided within minutes. After a few hours, the erythema and edema cleared.

TABLE 3

Formulation for treating allergic dermatitis resulting from exposure to urushiol.

| Ingredient | Percent by Weight |
|---|---|
| Water | 88.6% |
| Bovine Serum Albumin | 4.1% |
| Disodium ethylenediamine tetraacetate (DS EDTA) | 0.1% |
| Methyl Paraben | 0.2% |
| Hydroxypropylcellulose | 1.0% |
| Polyethylene glycol | 4.0% |
| Glycerine | 2.0% |

The formulation in Table 3 was prepared from commercially available ingredients: Bovine Serum Albumin is from Boval Company, L.P. of Cleburne, Texas; Disodium Edetate Dihydrate as Versene® is available from Dow Chemical, Midland, Mich.; methyl paraben is available from Malinckrodt Baker, Phillipsburg, N.Y.; Hydroxypropyl cellulose is available as Klucel® M from Hercules Incorporated of Wilmington, Del.; Polyethylene glycol is available as Carbowax™ from Dow Chemical, Midland, Mich. and Glycerine is available from Avatar Corporation, University Park, Ill.

EXAMPLE 2

A topical liquid was prepared using the formulation in Table 4 for treating allergic dermatitis.

A female with a known allergy to fire ant bites was stung multiple times by a red imported fire ant. Approximately 4 drops of the topical liquid was applied in a circular pattern to the affected area. The liquid was removed with water after 10 minutes. The pain ceased and no lesions developed.

TABLE 4

Formulation for treating allergic dermatitis resulting from exposure to isosolenopsin A.

| Ingredient | Percent by Weight |
|---|---|
| Water | 90.6% |
| Bovine Serum Albumin | 2.66% |
| Disodium ethylenediamine tetraacetate (DS EDTA) | 0.05% |
| Methyl Paraben | 0.1% |
| Hydroxypropylcellulose | 1.5% |
| Polyethylene glycol | 4.0% |
| Glycerine | 2.0% |

The composition in Table 4 was prepared using the commercially available ingredients described in Example 1 above.

It is understood that variations may be made in the foregoing without departing from the scope of the disclosure. Moreover, one or more of the above-described embodiments and/or variations may be combined in whole or in part with any one or more of the other above-described embodiments and/or variations.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims. In the claims, means-plus-function clauses are intended to cover the structures described herein as performing the recited function and not only structural equivalents, but also equivalent structures.

What is claimed is:

1. A method for treating oleoresin induced allergic dermatitis comprising:
   topically contacting an affected area with a composition consisting essentially of from about 2 to about 6 percent by weight of albumin for a sufficient amount of time to enable the albumin to provide a localized anti-inflammatory effect and
   removing the albumin from the affected area;
   wherein the composition minimizes the removal of protective lipids from the skin and removes oleoresin toxins from the dermal proteins of the skin by binding to oleoresin toxins in both native and oxidized states.

2. The method of claim 1, wherein the composition is a liquid, gel, cream, lotion, paste, ointment, foam, spray, mist, or aerosol to the affected area.

3. The method of claim 1, wherein the composition is provided as a coating on, or a filler in a dressing, substrate or patch.

4. The method of claim 1, wherein the albumin is a serum albumin.

5. The method of claim 1, wherein the composition further consisting essentially of a pharmaceutically active ingredient.

6. The method of claim 5, wherein the pharmaceutically active ingredient is selected from the group consisting of an analgesic, an antiasthmatic, an antimicrobial, an antipruritic, an antihistamine, an anti-inflammatory, an anti-skin wrinkling agent, a tanning active, a vasoconstrictor, a vasodilator, a vitamin substance, and mixtures thereof.

7. The method of claim 1, wherein the composition further consisting essentially of a drying agent.

8. The method of claim 1, wherein the composition further consisting essentially of a film former.

9. The method of claim 1, where the oleoresin is urushiol.

10. The method of claim 1, wherein the oleoresin is isosolenopsin A.

11. A method for treating oleoresin induced allergic dermatitis comprising:
topically contacting an affected area with a composition consisting of by weight from 2 to 6% of albumin, from 0.05 to 0.1% of a chelating agent, from 0.05 to 0.1% of a preservative, from 0.5 to 2% of a thickener, from 2 to 6% of a co-solvent, from 1.0 to 4.0% of an humectant, and a diluent, and
removing the composition from the affected area;
wherein the composition minimizes the removal of protective lipids of the skin and removes oleoresin toxins from the dermal proteins of the skin by binding to oleoresin toxins in both native and oxidized states.

12. A method for treating oleoresin induced allergic dermatitis comprising:
topically contacting an affected area with a composition consisting of by weight from 2 to 6% of a bovine serum albumin, from 0.05 to 0.1% of a chelating agent, from 0.05 to 0.1% of a preservative, from 0.5 to 2% of a thickener, from 2 to 6% of a co-solvent, from 1.0 to 4.0% of an humectant, and a diluent, and
removing the composition from the affected area;
wherein the composition minimizes the removal of protective lipids of the skin and removes oleoresin toxins from the dermal proteins of the skin by binding to oleoresin toxins in both native and oxidized states.

13. A method for treating oleoresin induced allergic dermatitis comprising:
topically contacting an affected area with a composition consisting of by weight from 2 to 6% of albumin, from 0.05 to 0.1% of disodium ethylenediamine tetraacetate, from 0.05 to 0.1% of methyl paraben, from 0.5 to 2% of hydroxypropylcellulose, from 2 to 6% of polyethylene glycol, from 1.0 to 4.0% of glycerine, and water, and
removing the composition from the affected area;
wherein the composition minimizes the removal of protective lipids of the skin and removes oleoresin toxins from the dermal proteins of the skin by binding to oleoresin toxins in both native and oxidized states.

14. A method for treating oleoresin induced allergic dermatitis comprising:
topically contacting an affected area with a composition consisting of by weight from 2 to 6% of bovine serum albumin, from 0.05 to 0.1% of disodium ethylenediamine tetraacetate, from 0.05 to 0.1% of methyl paraben, from 0.5 to 2% of hydroxypropylcellulose, from 2 to 6% of polyethylene glycol, from 1.0 to 4.0% of glycerine, and water, and
removing the composition from the affected area;
wherein the composition minimizes the removal of protective lipids of the skin and removes oleoresin toxins from the dermal proteins of the skin by binding to oleoresin toxins in both native and oxidized states.

15. A method for treating oleoresin induced allergic dermatitis comprising:
topically contacting an affected area with a composition consisting essentially of from about 2 to about 6 percent by weight of bovine serum albumin for a sufficient amount of time to enable the albumin to provide a localized anti-inflammatory effect and
removing the albumin from the affected area;
wherein the composition minimizes the removal of protective lipids from the skin and removes oleoresin toxins from the dermal proteins of the skin by binding to oleoresin toxins in both native and oxidized states.

* * * * *